(12) United States Patent
Lee (10) Patent No.: US 11,564,951 B2
(45) Date of Patent: Jan. 31, 2023

(54) MEDIUM COMPOSITION FOR CELL PROLIFERATION, SKIN REGENERATION, AND WRINKLE IMPROVEMENT COMPRISING, AS ACTIVE INGREDIENT, CONDITIONED MEDIUM OF PLURIPOTENT STEM CELLS, NEURAL STEM CELLS, OR EMBRYONIC FIBROBLASTS WHICH ARE ISOLATED FROM AVIAN EGGS

(71) Applicant: Jung Bok Lee, Wonju-si (KR)

(72) Inventor: Jung Bok Lee, Wonju-si (KR)

( * ) Notice: Subject to any disclaimer, the term of this patent is extended or adjusted under 35 U.S.C. 154(b) by 264 days.

(21) Appl. No.: 16/769,986

(22) PCT Filed: Oct. 10, 2018

(86) PCT No.: PCT/KR2018/011852
§ 371 (c)(1),
(2) Date: Jun. 4, 2020

(87) PCT Pub. No.: WO2019/112161
PCT Pub. Date: Jun. 13, 2019

(65) Prior Publication Data
US 2020/0384036 A1    Dec. 10, 2020

(30) Foreign Application Priority Data
Dec. 6, 2017    (KR) .................. 10-2017-0166745

(51) Int. Cl.
*A61K 35/57* (2015.01)
*A61K 8/98* (2006.01)
*A61Q 19/08* (2006.01)

(52) U.S. Cl.
CPC .............. *A61K 35/57* (2013.01); *A61K 8/982* (2013.01); *A61Q 19/08* (2013.01)

(58) Field of Classification Search
CPC ......... A61Q 19/08; A61Q 19/00; A61P 17/02; C12N 2502/088
See application file for complete search history.

(56) References Cited

FOREIGN PATENT DOCUMENTS

| CN | 106511387 A | * | 3/2017 |
|---|---|---|---|
| KR | 1020100096447 | | 9/2010 |
| KR | 1020150009898 | | 1/2015 |
| KR | 101830062 | | 2/2018 |
| KR | 101849631 | | 4/2018 |

OTHER PUBLICATIONS

B. Pain, et al., "Long-term in vitro culture and characterisation of avian embryonic stem cells with multiple morphogenetic potentialities", Development, (1996), pp. 1222339-1222348.
Hefzibah Eyal-Giladi et al., "From Cleavage to Primitive Streak Formation: A Complementary Normal Table and a New Look at the First Stages of the Development of the Chick", Developmental Biology, (1976), vol. 49, pp. 321-337.
Katherine Whalley, et al., "Changes in progenitor populations and ongoing neurogenesis in the regenerating chick spinal cord", Developmental Biology, (2009), vol. 332, pp. 234-245.
Korean Notice of Allowance—Korean Application No. 10-2017-0166745 dated May 28, 2020.
Rui Dai, et al., "Maintenance and Neuronal Differentiation of Chicken Induced Pluripotent Stem-Like Cells", Stem cell International, (2014), pp. 1-15.
International Search Report—PCT/KR2018/011852 dated May 30, 2019.
Written Opinion—PCT/KR2018/011852 dated May 30, 2019.
M. Mohiti-Asli et al., "Ibuprofen loaded PLA nanofibrous scaffolds increase proliferation of human skin cells in vitro and promote healing of full thickness incision wounds in vivo," Journal of Biomedical Materials Research B: Applied Biomaterials, 2015, pp. 1-13.

* cited by examiner

*Primary Examiner* — Qiuwen Mi
(74) *Attorney, Agent, or Firm* — Cantor Colburn LLP (57) ABSTRACT

The present invention relates to a medium composition for cell proliferation, skin regeneration, and wrinkle improvement that contains a conditioned medium of pluripotent stem cells (PSCs), neural stem cells (NSCs), and embryonic fibroblasts (FBs) as cells isolated from avian eggs as an active ingredient. Specifically, the conditioned medium of egg cells can fundamentally block contamination due to the use of animal serums, exhibits a proliferation effect of various cells containing human stem cells and skin cells without the possibility of transmission by infectious agents between heterogeneous species due to the use of support cells, and exhibits significant skin regeneration or wrinkle improvement effects, and thus the conditioned medium of egg cells can be usefully used for a medium composition for cell proliferation and a cosmetic composition for skin regeneration or wrinkle improvement.

9 Claims, 7 Drawing Sheets
Specification includes a Sequence Listing.

SEQUENCE LISTING

<160> NUMBER OF SEQ ID NOS: 14

<210> SEQ ID NO 1
<211> LENGTH: 19
<212> TYPE: DNA
<213> ORGANISM: Artificial sequence
<220> FEATURE:
<223> OTHER INFORMATION: primer

<400> SEQUENCE: 1
caacggaggc tatgggatg                                              19

<210> SEQ ID NO 2
<211> LENGTH: 20
<212> TYPE: DNA
<213> ORGANISM: Artificial sequence
<220> FEATURE:
<223> OTHER INFORMATION: primer

<400> SEQUENCE: 2

```
cgaatgagac gaggaggtga                                               20

<210> SEQ ID NO 3
<211> LENGTH: 20
<212> TYPE: DNA
<213> ORGANISM: Artificial sequence
<220> FEATURE:
<223> OTHER INFORMATION: primer

<400> SEQUENCE: 3
cagcagacct ctccttgacc                                               20

<210> SEQ ID NO 4
<211> LENGTH: 20
<212> TYPE: DNA
<213> ORGANISM: Artificial sequence
<220> FEATURE:
<223> OTHER INFORMATION: primer

<400> SEQUENCE: 4
ttccttgtcc cactctcacc                                               20

<210> SEQ ID NO 5
<211> LENGTH: 20
<212> TYPE: DNA
<213> ORGANISM: Artificial sequence
<220> FEATURE:
<223> OTHER INFORMATION: primer

<400> SEQUENCE: 5
caacgagcct acattgctaa                                               20

<210> SEQ ID NO 6
<211> LENGTH: 21
<212> TYPE: DNA
<213> ORGANISM: Artificial sequence
<220> FEATURE:
<223> OTHER INFORMATION: primer

<400> SEQUENCE: 6
ctcatctggg aactcacatt c                                             21

<210> SEQ ID NO 7
<211> LENGTH: 20
<212> TYPE: DNA
<213> ORGANISM: Artificial sequence
<220> FEATURE:
<223> OTHER INFORMATION: primer

<400> SEQUENCE: 7
taaaggcgag atggtgaaag                                               20

<210> SEQ ID NO 8
<211> LENGTH: 21
<212> TYPE: DNA
<213> ORGANISM: Artificial sequence
<220> FEATURE:
<223> OTHER INFORMATION: primer

<400> SEQUENCE: 8
acgctcctgg aagatagtga t                                             21

<210> SEQ ID NO 9
<211> LENGTH: 20
<212> TYPE: DNA
```

```
<213> ORGANISM: Artificial sequence
<220> FEATURE:
<223> OTHER INFORMATION: primer

<400> SEQUENCE: 9
agggccaaga cgaagacatc                                          20

<210> SEQ ID NO 10
<211> LENGTH: 21
<212> TYPE: DNA
<213> ORGANISM: Artificial sequence
<220> FEATURE:
<223> OTHER INFORMATION: primer

<400> SEQUENCE: 10
agatcacgtc atcgcacaac a                                        21

<210> SEQ ID NO 11
<211> LENGTH: 21
<212> TYPE: DNA
<213> ORGANISM: Artificial sequence
<220> FEATURE:
<223> OTHER INFORMATION: primer

<400> SEQUENCE: 11
tctggatgga ttgaagggac a                                        21

<210> SEQ ID NO 12
<211> LENGTH: 20
<212> TYPE: DNA
<213> ORGANISM: Artificial sequence
<220> FEATURE:
<223> OTHER INFORMATION: primer

<400> SEQUENCE: 12
ccaacacgtc ctctctcacc                                          20

<210> SEQ ID NO 13
<211> LENGTH: 20
<212> TYPE: DNA
<213> ORGANISM: Artificial sequence
<220> FEATURE:
<223> OTHER INFORMATION: primer

<400> SEQUENCE: 13
acccactcct ccacctttga                                          20

<210> SEQ ID NO 14
<211> LENGTH: 20
<212> TYPE: DNA
<213> ORGANISM: Artificial sequence
<220> FEATURE:
<223> OTHER INFORMATION: primer

<400> SEQUENCE: 14
tggtggtcca ggggtcttac                                          20
```

MEDIUM COMPOSITION FOR CELL PROLIFERATION, SKIN REGENERATION, AND WRINKLE IMPROVEMENT COMPRISING, AS ACTIVE INGREDIENT, CONDITIONED MEDIUM OF PLURIPOTENT STEM CELLS, NEURAL STEM CELLS, OR EMBRYONIC FIBROBLASTS WHICH ARE ISOLATED FROM AVIAN EGGS

TECHNICAL FIELD

The present invention relates to a medium composition for promoting proliferation of cells including human stem cells, human mesenchymal stem cells, or human skin cells that contains a conditioned medium of pluripotent stem cells (PSCs), neural stem cells (NSCs), or embryonic fibroblasts (FBs) which are cells isolated from avian eggs as active ingredients.

BACKGROUND ART

Stem cells are cells that have the ability to differentiate into various cells through a suitable environment and stimulation and have self-proliferation ability. Three kinds of embryonic stem cells (ESCs) isolated from early embryos, embryonic germ cells (EG cells) isolated from primitive germ cells in an embryonic period, and induced pluripotent stem cells are well known as pluripotent stem cells (PSCs), and particularly, the embryonic stem cell means egg blastoderm derived pluripotent stem cells (PSCs). The hematopoietic stem cells (HSCs), the mesenchymal stem cells (MSCs), and the neural stem cells (NSCs) are adult stem cells and well-known as multipotent stem cells (MSCs). The stem cells have the potential to develop into cells with characteristic phenomena and specialized functions, and thus become a research target as cell resources for functional recovery for various organs.

On the other hand, unlike differentiated cells in which cell division is stopped, the stem cells can produce cells same as themselves by cell division (self-renewal) to have the proliferation (expansion) properties and can differentiate into specific cells under a differentiation stimulus. In addition, stem cells can differentiate into other cells under other environments or different stimuli to have plasticity in differentiation. There are two method for obtaining stem cells. One is to obtain stem cells from embryos generated from fertilized eggs (embryonic stem cells), and the second is to collect stem cells stored in each part of the adult body (adult stem cells). Though the cells are different from each other in terms of functions, embryonic stem cells or adult stem cells have the characteristics of being able to differentiate into various kinds of cells.

The dermis mainly consists of collagen and elastin fibers, which have a role of supporting the skin. Therefore, if a problem occurs in the dermis, wrinkles are formed, and skin elasticity disappears, so skin aging progresses. Collagen is known to play the most important role in skin regeneration, skin moisture, wound healing, and wrinkle improvement, and is produced from fibroblasts. Collagen has a function to contain a large amount of moisture and has a role of supplying moisture to the dermis. When aging progresses, the water-containing function of collagen decreases to increase wrinkles. Collagen also has an effect of wound healing by filling a wound area with continuous collagen production by the fibroblasts when a wound is formed. The dermis consists mainly of collagen and elastin fibers, which has a role of supporting the skin. Therefore, when a problem occurs in the dermis, wrinkles are formed, and skin elasticity disappears, so skin aging progresses. Collagen is known to play the most important role in skin regeneration, skin moisture, wound healing, and wrinkle improvement, and is produced from fibroblasts. Collagen has a function to contain a large amount of moisture and has a role of supplying moisture to the dermis. When aging progresses, the water-containing function of collagen decreases to increase wrinkles. Collagen also has an effect of wound healing by filling a wound area with continuous collagen production by the fibroblasts when a wound is formed.

In view of this, the present inventors diligently tried to develop a novel use of the conditioned medium of egg-derived stem cells and found that, since the conditioned medium of bird egg-derived stem cells significantly proliferates human stem cells, skin cells, and the like even without feeder cells and exhibits remarkable skin regeneration and wrinkle improvement effects, the conditioned medium of egg-derived stem cells can be usefully used as a medium composition for cell proliferation or as an active ingredient of a cosmetic composition for skin regeneration and wrinkle improvement, and completed the present invention.

SUMMARY OF INVENTION

Technical Problem

An object of the present invention is to provide a medium composition for cell proliferation containing a conditioned medium of avian egg-derived stem cells as an active ingredient.

The present invention is to provide a cosmetic composition for skin regeneration and wrinkle improvement containing a conditioned medium of avian egg-derived cells as an active ingredient.

Solution to Problem

In order to achieve the above object, the present invention provides a medium composition for cell proliferation containing a conditioned medium of avian egg-derived stem cells as an active ingredient.

The present invention provides a pharmaceutical composition for treating a wound containing a conditioned medium of avian egg-derived cells as an active ingredient.

The present invention provides a cosmetic composition for skin regeneration or wrinkle improvement containing a conditioned medium of avian egg-derived cells as an active ingredient.

Advantageous Effects of Invention

The conditioned medium of avian egg stem cells according to the present invention can fundamentally block contamination due to the use of animal serums, exhibits a proliferation effect of various cells including human stem cells and skin cells without the possibility of transmission by infectious agents between heterogeneous species due to the use of support cells, and exhibits significant skin regeneration or wrinkle improvement effects, and thus the conditioned medium of egg stem cells can be usefully used for a medium composition for cell proliferation and a cosmetic composition for skin regeneration or wrinkle improvement.

BRIEF DESCRIPTION OF DRAWINGS

FIGS. 1A to 1D are diagrams showing pluripotent stem cells derived from a fertilized egg blastoderm;

DESCRIPTION OF EMBODIMENTS

Hereinafter, the present invention is described in more detail.

The present invention provides a medium composition for cell proliferation, including a conditioned medium of avian egg-derived stem cells as an active ingredient.

The eggs described above are eggs of a bird, and examples of the bird include taxonomically all species, subspecies, or genus (rass) of the class Aves such as chickens, turkeys, ducks, wild geese, quails, pheasants, sparrows, pigeons, parrots, finches, falcons, crows, ostriches, emus, and cassowary, but the present invention is not limited thereto. Particularly preferred examples include Gallus gallus, or White Leghorn, Brown Leghorn, Barred-Rock, Sussex, California Gray, and Italian Partridge-Colored which are kinds of chickens.

Examples of the egg-derived stem cell according to the present invention include pluripotent stem cells obtained from the blastoderm of the fertilized egg of an embryo corresponding to stage-X or XI at the stage of development of Eyal-Giladi and Kochav (EG & K, 1976), pluripotent cells obtained by collecting blood from embryos that are obtained by culturing fertilized eggs in an incubator at the condition of 38° C. for three to five days to reach stages 14 to 17 of the development stage of H & H (Hamburger and Hamilton, 1951), embryonic germ cells (EGCs) isolated from gonads that are obtained by culturing fertilized eggs in an incubator at the condition of 38° C. for five to six days and formed at stage 28 of H & H (Hamburger and Hamilton, 1951), and induced pluripotent stem cells (iPSCs) obtained by treating, with Yamanaka transcription factors (OCT4, Sox2, KIF-4, and c-Myc), embryonic fibroblasts (EFs) obtained from muscle tissues obtained by culturing fertilized eggs at the condition of 38° C. for 11 days or obtained by overexpressing miRNA-302 clusters, but the present invention is not limited thereto.

The conditioned medium refers to a medium obtained by exchanging cells with a serum-free medium when the cells reach an exponential phase, which is the peak of cell division, and then collecting only the culture medium. This refers to the use of unknown growth factors and cytokine extracted from dividing cells into the medium. According to an embodiment, the conditioned medium includes a solution obtained by culturing egg stem cells in a serum-free medium and removing the stem cells, and thus may richly contain materials such as growth factors and cytokine derived from the egg stem cells.

The conditioned medium can be produced by first culturing egg stem cells in a medium including a growth factor or the like and culturing the egg stem cells in a serum-free medium, but the first pre-culturing step may not be performed, or the conditioned medium can be produced by stem cells after egg stem cells are cultured in a basic medium.

The medium composition for cell proliferation is preferably any one medium for proliferation of cells selected from the group consisting of human stem cells, somatic cells, and skin cells, the human stem cell is preferably embryonic stem cells or adult stem cells, and the adult stem cells can be used any one selected from the group consisting of bone marrow-derived, adipose-derived, cord blood-derived, blood-derived, liver-derived, skin-derived, gastrointestinal-derived, placenta-derived, nerve-derived, adrenal-derived, epithelial-derived, and uterine-derived stem cells.

In a specific example of the present invention, the present inventors produced a conditioned medium of egg stem cells by isolating neural stem cells and pluripotent stem cells from chicken eggs (see FIGS. 1A to 1D, and FIGS. 2A and 2B) and culturing the cells in a basic medium.

Figure 3A:
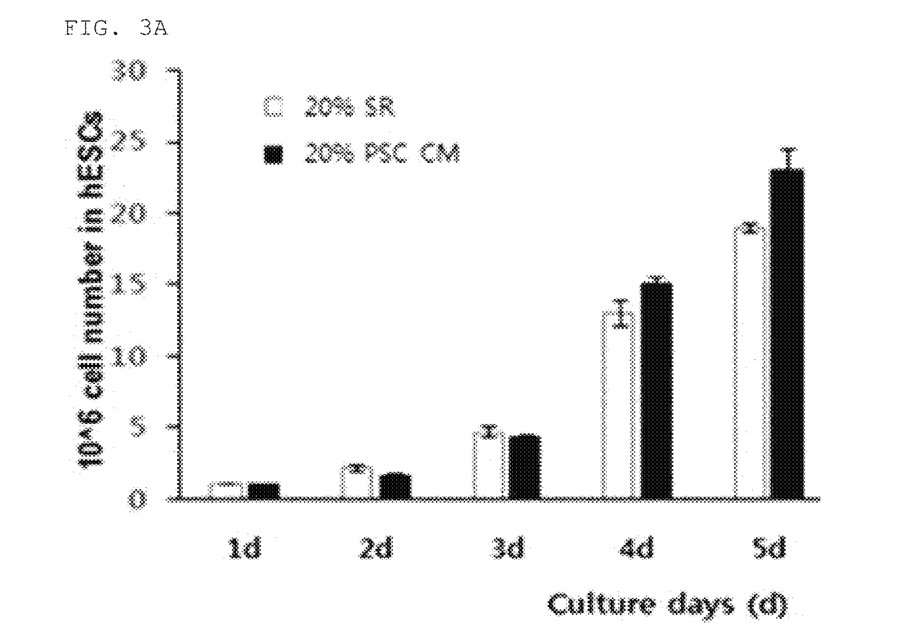
FIGS. 3A and 3B are diagrams for confirming effects of proliferation of human embryonic stem cells and human mesenchymal stem cells of the conditioned mediums of egg-derived stem cells.
Figure 3B:
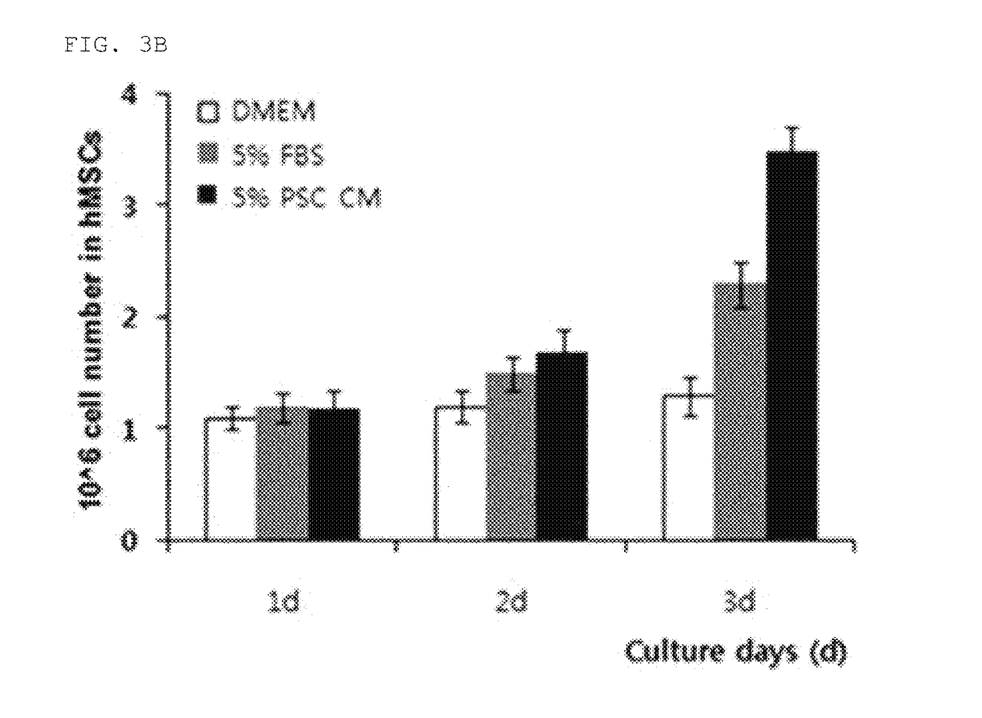
Figure 4:
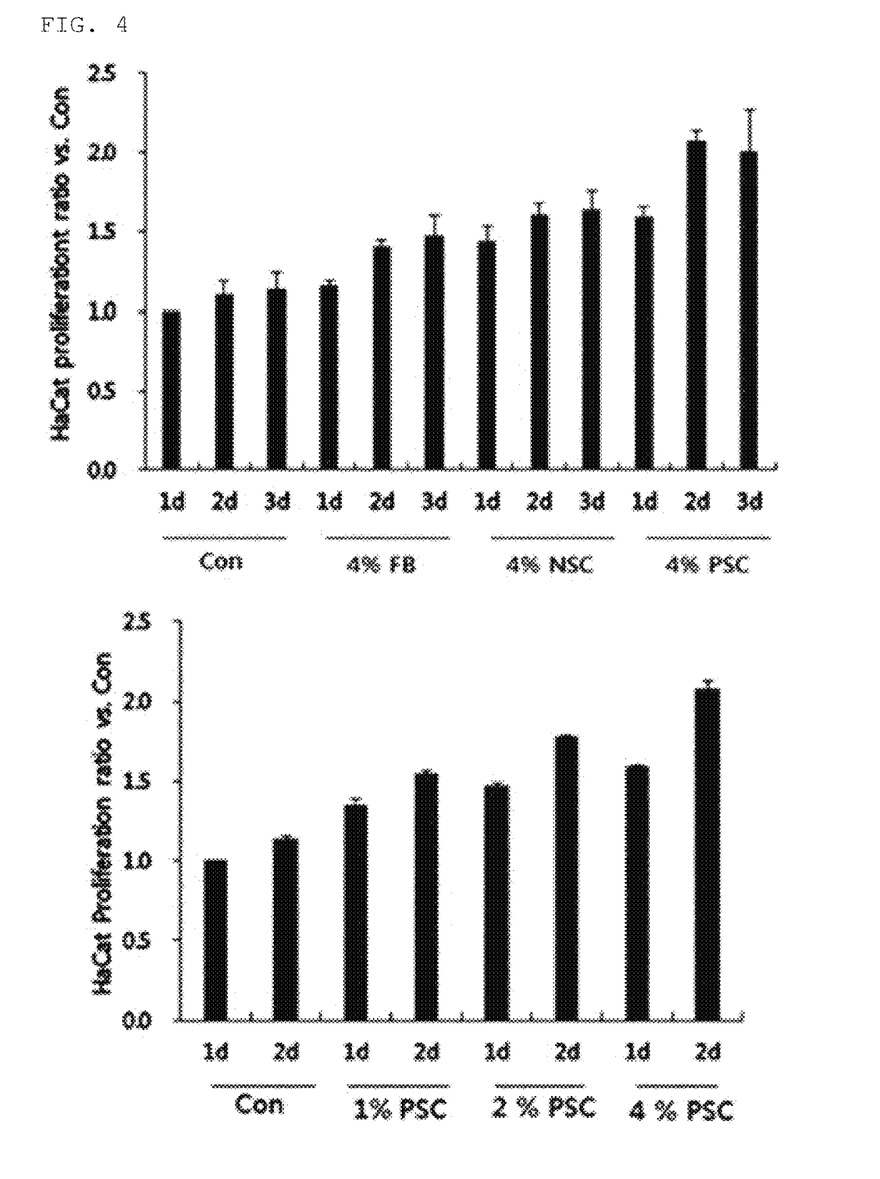
FIG. 4 is a diagram for confirming an effect of skin cell proliferation of the conditioned mediums of egg-derived stem cells.

In order to confirm the cell proliferation effect of the conditioned medium of egg stem cells of the present invention, human stem cells or skin cells were cultured in a basic medium including the conditioned medium of egg stem cells, and as a result, it was confirmed that significant proliferation ability of human stem cells or skin cells is exhibited even without addition of animal serums and support cells (see FIGS. 3A and 3B, and FIG. 4).

Therefore, the conditioned medium of avian egg stem cells according to the present invention can fundamentally block contamination due to the use of animal serums and thus can be usefully used as a medium composition for proliferation of various cells including human stem cells and skin cells without the possibility of transmission by infectious agents between heterogeneous species due to the use of support cells.

The present invention provides a pharmaceutical composition for treating skin wounds containing a conditioned medium of avian egg-derived cells as an active ingredient.

The avian egg-derived cells are any one selected from the group consisting of pluripotent stem cells, neural stem cells, and fibroblasts.

The wound of the present invention refers to a state in which a living body is damaged and may include a damage on any part of an individual such as tissues that consist inner or outer surfaces of the living body.

The conditioned medium of avian egg-derived cells promotes skin cell proliferation and has activity in a wound treatment and skin regeneration. The content of the active ingredient of the present invention may be 0.1% to 100% by weight with respect to the total weight of the composition.

In a specific example of the present invention, the present inventors cultured HaCaT (keratinocyte, Thermo) skin cells in an egg-derived cell culture medium for a certain period of time and compared the growth rate in order to confirm the skin cell proliferation ability in the conditioned medium of egg-derived cells and as a result, confirmed effective skin cell proliferation ability (see FIG. 4).

In conclusion, it was confirmed that the skin cell proliferation effect is excellent when skin cells are cultured in the conditioned medium of avian egg-derived cells according to the present invention, and thus the conditioned medium of avian egg-derived cells can be used as an active ingredient of a pharmaceutical composition for treating skin wounds.

The pharmaceutical composition including the conditioned medium of egg-derived cells according to the present invention may further include a suitable carrier, an excipient, and a diluent which are generally used, in addition to the conditioned medium of egg-derived cells which is the active ingredient. In addition, in the production of the pharmaceutical composition, solid or liquid additives for formulation can be used. The additives for formulation may be either organic or inorganic.

Examples of excipients include lactose, sucrose, white sugar, glucose, corn starch, starch, talc, sorbit, crystalline cellulose, dextrin, kaolin, calcium carbonate, silicon dioxide, and the like. Examples of binders include polyvinyl alcohol, polyvinyl ether, ethyl cellulose, methyl cellulose, Arabic gum, tragacanth, gelatin, shellac, hydroxypropyl cellulose, hydroxypropyl methyl cellulose, calcium citrate, dextrin, pectin, and the like. Examples of lubricants include magnesium stearate, talc, polyethylene glycol, silica, cured vegetable oil, and the like. Any colorant can be used as long as the colorant is generally permitted to be added to pharmaceuticals. Tablets and granules of these can be appropriately coated by sugar coating, gelatin coating, or the like as necessary. Preservatives, antioxidants, and the like can be added as necessary.

The pharmaceutical composition of the present invention may be produced in any formulation generally produced in the art (for example, Remington's Pharmaceutical Science, the latest edition; Mack Publishing Company, Easton Pa.). The form of the formulation is not particularly limited, but may preferably be an external preparation. The external preparations of the present invention include forms of general external preparations such as sheet, liquid coating, spray, lotion, cream, patch, powder, penetrating pad, spray, gel, paste, liniment, ointment, aerosol, powder, suspension, transdermal absorbers, and the like. These formulations are described in a document [Remington's Pharmaceutical Science, 15th Edition, 1975, Mack Publishing Company, Easton, Pa. 18042 (Chapter 87: Blaug, Seymour)], which is a prescription generally known to all pharmaceutical chemistries.

In the external preparation of the present invention, a pharmaceutically acceptable carrier differs depending on the formulation thereof. However, examples thereof include hydrocarbons such as vaseline, liquid paraffin, gelled hydrocarbons (also referred to as plastibase), and the like; animal and vegetable oil such as medium chain fatty acid triglyceride, lard, hard fat, cacao butter, and the like; higher fatty acid alcohols such as cetanol, stearyl alcohol, stearic acid, isopropyl palmitate, and the like, and fatty acids and esters thereof; water-soluble base materials such as macrogol (polyethylene glycol), 1,3-butylene glycol, glycerol, gelatin, white sugar, sugar alcohol, and the like; emulsifiers such as glycerin fatty acid ester, polyoxyl stearate, polyoxyethylene cured castor oil, and the like; adhesives such as acrylic acid ester, sodium alginate, and the like; propellants such as liquefied petroleum gas, carbon dioxide, and the like; and preservatives such as paraoxybenzoic acid esters and the like. The external preparation of the present invention can be produced with these by a general method. In addition to these, stabilizers, fragrances, colorants, pH adjusters, diluents, surfactants, preservatives, antioxidants and the like may be added as necessary. The external preparation of the present invention can be applied to a local wound by a general method. The external preparation according to the present invention can be used by being adhered to a solid support such as a wound peeling cover of a general plaster. As an aspect of the present invention, the solid support is first coated with an adhesive layer to improve the adhesion of the culture medium to the solid support. Examples of the adhesive include polyacrylate and cyanoacrylate.

The pharmaceutically effective amount of the present invention may vary depending on wound types of patients, application sites, the number of treatments, treatment time, formulations, patient's conditions, and types of adjuvants. The amount of use is not particularly limited, but, generally, a daily effective amount of the pharmaceutical composition of the present invention may be 1 to 50 µl/cm$^2$ when a composition including a conditioned medium of egg-derived cells is applied to wounds, and preferably 5 to 20 µl/cm$^2$. The above daily amount may be administered once a day, may be administered by being divided into 2-3 times a day at appropriate intervals, or may be intermittently administered at intervals of several days. However, the use amount of the pharmaceutical composition of the present invention is determined according to various relevant factors such as administration routes, patients' ages, genders, weights, severity of patients, types of wounds, application sites, the number of treatments, treatment time, formulations, patient conditions, and types of supplements, and thus the above effective amount does not limit the scope of the present invention in any aspects.

The present invention provides a cosmetic composition for skin regeneration or wrinkle improvement including the conditioned medium of avian egg-derived cells as an active ingredient.

The avianegg-derived cells are preferably any one selected from the group consisting of pluripotent stem cells, neural stem cells, and fibroblasts.

The conditioned medium of egg-derived cells of the present invention effectively proliferates skin cells, increases expression of collagen genes relating to skin wrinkles and moisturization, and increases hyaluronic acid production, increases expression of elastin genes, and thus can be used as a cosmetic composition for skin regeneration or wrinkle improvement.

The cosmetic composition for improving skin condition including the conditioned medium of egg-derived cells of the present invention may include a carrier acceptable in cosmetic preparations. Here, the "carrier acceptable in cosmetic preparations" refers to already known and used compounds or compositions or compounds or compositions to be developed in the future that may be included in cosmetic preparations and do not have toxicity, instability, or irritation being not adaptable to human bodies when in contact with skin. The content of the carrier may be about 1% to 99.99% by weight with respect to the total weight of the cosmetic composition of the present invention, and preferably 90% to 99.99% by weight with respect to the weight of the composition. However, the above ratio may differ depending on the formulation described below for producing the cosmetic composition of the present invention, specific application site thereof (face, neck, or the like), preferred application amounts thereof, and the like, and thus the above ratio does not limit the scope of the present invention in any aspects.

Examples of the carrier include alcohol, oil, surfactants, fatty acid, silicone oil, wetting agents, moisturizing agents, viscous modifiers, emulsions, stabilizers, ultraviolet scattering agents, ultraviolet absorbers, colorants, and fragrances. Since compounds and compositions that can be used as alcohol, oil, surfactants, fatty acid, silicone oil, wetting agents, moisturizing agents, viscous modifiers, emulsions, stabilizers, ultraviolet scattering agents, ultraviolet absorbers, colorants, fragrances, and the like are already known in the art, those skilled in the art can select and use appropriate corresponding materials and compositions. As an embodiment of the present invention, the cosmetic composition according to the present invention may include glycerin, butylene glycol, propylene glycol, polyoxyethylene cured castor oil, ethanol, triethanol amine, and the like, in addition to the egg-derived stem cell culture medium, and may include minute amounts of preservatives, flavoring agents, coloring agents, purified water, and the like, as necessary. The cosmetic composition according to the present invention may be produced in various forms and can be produced, for example, in forms of skin lotion, essence, gel, emulsion, lotion, cream (oil-in-water type, water-in-oil type, multi-phase), solutions, suspensions (anhydrous and water-based), anhydrous products (oil and glycol-based), gels, masks, packs, powder, or capsules with coatings such as gelatin (soft capsules and hard capsules). The skin in the present invention is a concept that includes the face as well as the scalp and the whole body. Examples of the cosmetic composition that can be applied to the scalp include shampoo, conditioners, treatments, and hair growth solutions, and can be produced in various forms for the use as body cleansers or the like that can be applied to the whole body. The method of producing the cosmetic composition for skin regeneration or skin wound improvement containing the egg-derived stem cell culture medium according to the present invention is not limited to the above production method, and a person having ordinary knowledge in the technical field to which the present invention pertains can produce the cosmetic composition according to the present invention even by a method obtained by modifying a part of the above production method.

Particularly, the cosmetic composition for skin regeneration or the cosmetic composition for wrinkle improvement can be produced in forms of general emulsifying formulations and solubilizing formulations by using a generally known production method in addition to the production method particularly described in the present invention. When the cosmetic compositions in emulsifying formulations and solubilizing formulations are produced, examples of cosmetics in emulsifying formulations include nutrient skin lotion, cream, essence, and the like, and examples of cosmetics in solubilizing formulations include softening skin lotion. By containing a dermatologically acceptable medium or base, the cosmetic compositions can be prepared in the form of adjuvants that can be applied locally or systemically, which is commonly used in the dermatology field. As the suitable cosmetic formulations, the cosmetic compositions can be provided, for example, in forms of solutions, gels, solid or paste anhydrous products, emulsions obtained by dispersing an oil phase in a water phase, suspensions, microemulsions, microcapsules, microgranules, forms of ionic (liposomes) and nonionic vesicle dispersants, cream, skin lotion, lotion, powder, ointments, spray, or concealer sticks. The cosmetic compositions can also be produced in the form of a foam or in the form of aerosol composition further containing a compressed propellant.

The cosmetic composition for skin regeneration or the cosmetic composition for wrinkle improvement according to the present invention may further include adjuvants generally used in the cosmetic or dermatological field such as fatty substances, organic solvents, solubilizing agents, thickeners, gelling agents, softeners, antioxidants, suspending agents, stabilizers, foaming agents, air fresheners, surfactants, water, ionic or nonionic emulsifiers, filling, metal ion blockers, chelating agents, preservatives, vitamin, blocking agents, wetting agents, essential oil, dyes, pigments, hydrophilic or lipophilic active agents, lipid vesicles, and any other ingredients generally used in cosmetics. The above ingredients may be introduced in an amount generally used in the dermatological field. The cosmetic composition according to the present invention includes forms of functional cosmetics for skin convergence, anti-inflammatory, wounds, wound healing, anti-aging, and the like.

Hereinafter, the present invention is described in detail with reference to examples and experimental examples.

However, the following examples and experimental examples merely exemplify the present invention, and the contents of the present invention are not limited to the examples and the experimental examples described below.

<Example 1> Isolation of Stem Cell from Avian Egg Cells and Culture

<1-1> Isolation of Neural Stem Cells from Avian Eggs and Culture

Neural stem cells were isolated and cultured by using eggs of White Leghorn, which is a kind of Red junglefowl.

Specifically, the fertilized egg was cultured in the condition of 38° C. for eight days, the spinal canal was sliced into 1 mm and treated with enzyme (0.01% papain (sigma), 0.01% DNA I), PBS buffer was added, the centrifugation was performed at 800 g for 3 minutes, the supernatant was removed, and the resultant was incubated for one week in the neurobasal A medium containing growth factors of EGF, bFGF, and insulin, to obtain a spherical neuronal cell mass. For a specific culture method, Whalley W et al., (2009), Developmental Biology 332: 234-245 was referred to.

<1-2> Isolation of Pluripotent Stem Cells from Blastoderms of Avian Eggs and Culture The pluripotent stem cell of the present invention means an embryonic stem cell (ESC) isolated from blastoderm cells of fertilized eggs and cultured and means a cell having OCT4, NANOG, SOX2, and alkaline phosphatase activity.

Specifically, fertilized eggs of White or Brown Leghorn, which is one type of chicken, were used. The blastoderms of the embryo at the development stage according to Eyal-Giladi and Kochav (EG & K, 1976), that is, stage-X or stage-XI were cut out by using surgical scissors. Viteline membranes and egg yolks of the cut blastoderms were removed in the PBS buffer, and the embryonic stem cells were isolated from the blastoderm with pluripotent. For embryonic stem cell growth, the cells were co-cultured with chicken embryonic fibroblast cells or STO cells of which the growth was inhibited by treatment with mitomycine C (10 ug/ml) for two hours. For the specific culture method, Eyal-Giladi and Kochav (1976), Dev Biol. 49:321-37 and Pain B et al. (1996), Development 122:2339-2348 were referred to.

<1-3> Isolation of Embryonic Fibroblasts from Avian Eggs and Culture

Eggs of White Leghorn, which is a kind of Red junglefowl, were used. Tissues obtained by culturing the fertilized eggs at 37° C. to 38° C. for four days were obtained, the heads and intestines were removed, and then the resultant was treated with enzymes (Trypsin-EDTA). DMEM containing 105% FBS was added, centrifugation was performed at 800 g for three minutes, the supernatant was removed, and the resultant was cultured in 10% DMEM medium for a long period of time to obtain embryonic fibroblasts (FBs). For the specific culturing method, Dai R et al (2014). Stem cell international 2014:1-15 was referred to.

<Example 2> A Conditioned Medium of Avian Egg Stem Cells

A conditioned medium was produced by using the pluripotent stem cells or the neural stem cells which are the egg-derived stem cells obtained in <Example 1> and the fibroblasts.

Specifically, the pluripotent stem cells, neural stem cells, or fibroblasts were cultured for three days in the DMEM/F12 medium which was the basic medium, the pluripotent stem cells, the neural stem cells, or the fibroblasts were removed to collect only the culture medium, and finally the conditioned medium of avain egg stem cells and the avain fibroblast conditioned medium were produced.

<Experimental Example 1> Confirmation of Stem Cells Isolated from Avain Egg Cells Stem cell ability of the egg-derived stem cells isolated and cultured in <Example 1> described above were confirmed. The pluripotent stem cells express alkaline phosphatase activity and OCT4, SOX2, and NANOG genes, which are marker genes, the neural stem cells express alkaline phosphatase activity and Nestin and SOX9, which are marker genes, and thus the stem cell ability of the egg-derived stem cells were confirmed by alkaline phosphatase staining, RT-PCR, or immunochemical staining.

For alkaline phosphatase staining, Naphtol-AS-MA-Phosphate (Sigma N5000) and Fast Red TR salt (Sigma F2768) were used in tris-maleate buffer containing 10% $MgCl_2$. The gene expression of OCT4, NANOG, and Nestin was performed with RT-PCR, and anti-mouse Oct4 (Santa Cruz) and Cy3-anti-mouse IgG were used as the antibody OCT4 used for immunostaining. Primers used in RT-PCR are shown in Table 1 below.

TABLE 1

| Gene | Forward primer | Reverse primer |
| --- | --- | --- |
| cSOX2 | 5'-CAACGGAGGCT ATGGGATG-3' (SEQ ID NO: 1) | 5'-CGAATGAGACG AGGAGGTGA-3' (SEQ ID NO: 2) |
| cNANOG | 5'-CAGCAGACCTC TCCTTGACC-3' (SEQ ID NO: 3) | 5'-TTCCTTGTCCC ACTCTCACC-3' (SEQ ID NO: 4) |
| cNestin | 5'-CAACGAGCCTA CATTGCTAA-3' (SEQ ID NO: 5) | 5'-CTCATCTGGGA ACTCACATTC-3' (SEQ ID NO: 6) |
| cGAPDH | 5'-TAAAGGCGAGA TGGTGAAAG-3' (SEQ ID NO: 7) | 5'-ACGCTCCTGGA AGATAGTGAT-3' (SEQ ID NO: 8) |

Figure 1A:
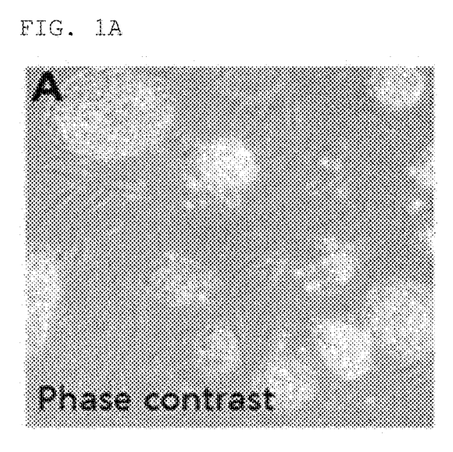
FIG. 1A is a diagram showing formation of colonies.
Figure 1B:
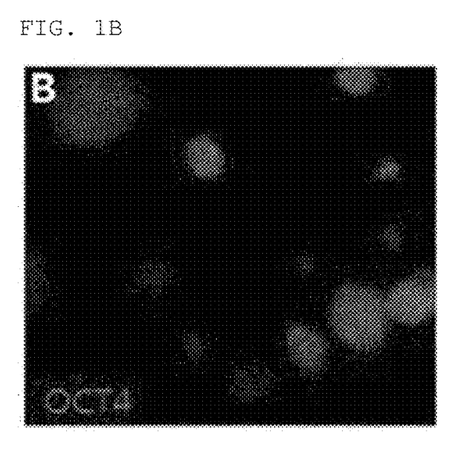
FIG. 1B is a diagram for confirming that the OCT4 gene is expressed by immunocytostaining.
Figure 1C:
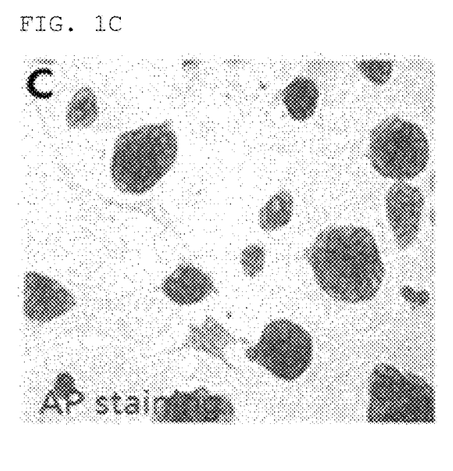
FIG. 1C is a diagram for confirming activity of alkaline phosphatase.
Figure 1D:
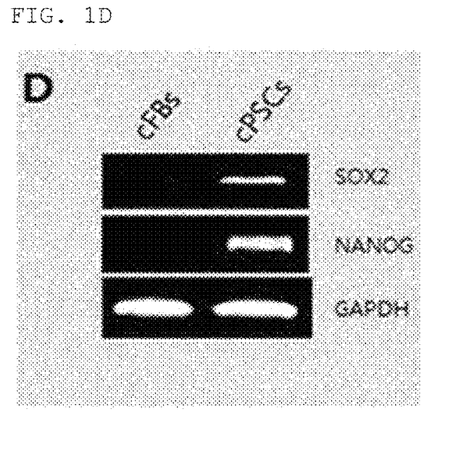
FIG. 1D is a diagram for confirming whether SOX2 and NANOG, which are markers of a pluripotent stem cell, are expressed.
Figure 2A:
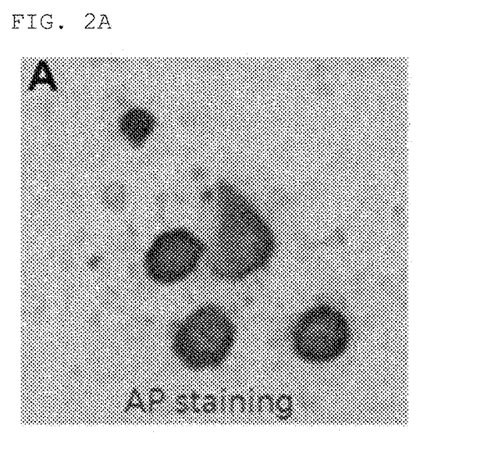
FIG. 2A is a diagram for confirming alkaline phosphatase activity of an egg-derived neural stem cell.
Figure 2B:
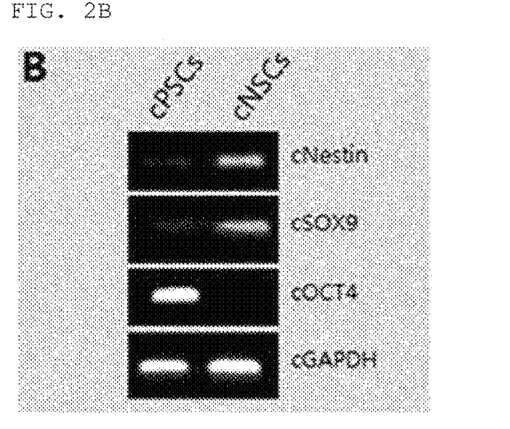
FIG. 2B is a diagram for confirming whether Nestin and SOX9, which are markers of a neural stem cell, is expressed.

As a result, as shown in FIGS. 1A to 1D, it was confirmed that pluripotent stem cells isolated from fertilized egg blastoderms form colonies (FIG. 1A), express the OCT4 gene (FIG. 1B), and exhibit alkaline phosphatase activity (FIG. 1C), and the pluripotent stem cell marker gene were significantly expressed compared with the embryonic fibroblasts (FIG. 1D). In addition, as shown in FIGS. 2A and 2B, it was confirmed that the egg-derived neural stem cells also exhibited alkaline phosphatase activity (FIG. 2A), and Nestin and SOX9, which were the neural stem cell markers, were significantly expressed (FIG. 2B).

Therefore, it was confirmed that the egg-derived stem cells isolated and cultured in <Example 1> were pluripotent stem cells and neural stem cells, respectively.

<Experimental Example 2> Confirmation of Cell Proliferation Ability of a Conditioned Medium of Avian Egg Stem Cells In order to confirm the human stem cell proliferation ability of the conditioned medium of avian egg stem cells, the human embryonic stem cells or the mesenchymal stem cells were cultured in DMEM/F12 medium containing a Serum Replacer (20%) (SR) and the conditioned medium of egg-derived pluripotent stem cells produced in <Example 2> (PCS-CM), respectively, and results thereof were compared and analyzed.

Specifically, the human embryonic stem cells (hESCs) were cultured in DMEM/F12 containing 20% Serum replace (Gibco) as a control. In the experimental group, the cells were cultured in DMEM/F12 medium containing the conditioned medium of egg-derived pluripotent stem cells (20%) produced in <Example 2>. The experiment proceeded for 5 days in total and the growth rate are shown (FIG. 3A). Further, the human mesenchymal stem cells were cultured in a medium containing 10% FBS, $1\times10^6$ of the cultured cells were seeded in a 60-mm dish, and the cells were cultured for 3 days by using a DMEM medium not containing FBS as Control Group 1, a DMEM medium containing 5% FBS as Control Group 2, and a DMEM medium containing 5% of the conditioned medium of egg-derived pluripotent stem cells produced in <Example 2> (5% PSC CM) as the experimental group, to measure the growth rate (FIG. 3B).

As a result, as shown in FIGS. 3A and 3B, it was confirmed that the proliferation of the human embryonic stem cells or the mesenchymal stem cells in the basic medium containing the conditioned medium of egg-derived pluripotent stem cells of the present invention was remarkably excellent (FIGS. 3A and 3B).

Therefore, it was confirmed that the conditioned medium of egg stem cells of the present invention can be used for the medium composition for stem cell proliferation.

<Experimental Example 3> Confirmation of Skin Cell Proliferation Ability of a Conditioned Medium of Avian Egg Stem Cells In order to confirm the skin cell proliferation ability of the conditioned medium of avian egg stem cells, skin cells were cultured in basic mediums containing the conditioned mediums of the fibroblasts, the neural stem cells, and the pluripotent stem cells isolated in <Example 1> in the concentration of 4%.

Specifically, HatCat cells which were skin cells were cultured in 10% FBS DMEM medium and then cultured in DMEM not containing FBS for one day to inhibit the cell growth. A DMEM medium not containing FBS was set as a control group, and as an experimental group, conditioned mediums of fibroblasts, neural stem cells, and pluripotent stem cells were added to a DMEM medium not containing FBS in the concentration of 4%, and then the growth rates of one day to three days were confirmed.

As a result, as shown in FIG. 4, in the conditioned mediums of the neural stem cells and the pluripotent stem cells, HaCaT cells were significantly proliferated compared with the non-treated control group, and an effect of proliferating HaCaT cells in the fibroblast conditioned medium was also confirmed (FIG. 4).

Tests were performed with reducing the content of the conditioned medium of pluripotent stem cells exhibiting a significant effect to 4%, 2%, to 1%, and as a result, it was confirmed that a significant proliferation effect was exhibited also in the addition concentration of 2% or less compared with the control group (FIG. 4).

<Experimental Example 4> Confirmation of Skin Regeneration and Wrinkle Improvement Effects of Bird a Conditioned Medium of Avian Stem Cells The skin regeneration and wrinkle improvement effects of the conditioned medium of avian egg stem cells were confirmed.

Specifically, skin cells (HaCaT) were cultured for two days in DMEM basic mediums containing conditioned mediums of the fibroblasts, the neural stem cells, and the pluripotent stem cells isolated in <Example 1> in the concentration of 4%, whether collagen genes (COLA1(collagen type I α1; NM_000088.3), COLA2(collagen type I α2; NM_000089.3)) relating to the wrinkle improvement was expressed was confirmed with expression degrees using qPCR, and skin cells were cultured in the DMEM basic medium as the control group, to confirm whether the collagen genes were expressed.

In order to confirm whether the conditioned medium of avian egg stem cells was related to the hyaluronic acid synthesis relating to the skin wrinkles and the moisturization, expression of hyaluronic acid synthetase 2 (HAS2), which was hyaluronic acid synthetase, and elastin genes were confirmed, and the production amount of Hyaluronic acid was measured by using the HA assay Elisa kit.

Specifically, $10^5$ cells of HaCat cells were seeded in a 60-mm dish and cultured in a DMEM medium containing 10% FBS, the cell growth was stopped for 24 hours by using a basic medium not containing serums, the cells were added to a medium containing 0% to 4% of the conditioned medium of the fibroblasts or the pluripotent stem cells and cultured for 48 hours, and expression of Hyaluronic acid synthetase-2 (HAS-2) was confirmed.

Meanwhile, primers used in this experiment are shown in Table 2 below.

TABLE 2

| Gene | Forward primer | Reverse primer |
| --- | --- | --- |
| COLA1 | AGGGCCAAGACGAAGACATC (SEQ ID NO: 9) | AGATCACGTCATCGCACAACA (SEQ ID NO: 10) |
| COLA2 | TCTGGATGGATTGAAGGGACA (SEQ ID NO: 11) | CCAACACGTCCTCTCTCACC (SEQ ID NO: 12) |
| GAPDH | ACCCACTCCTCCACCTTTGA (SEQ ID NO: 13) | TGGTGGTCCAGGGGTCTTAC (SEQ ID NO: 14) |

Figure 5A:
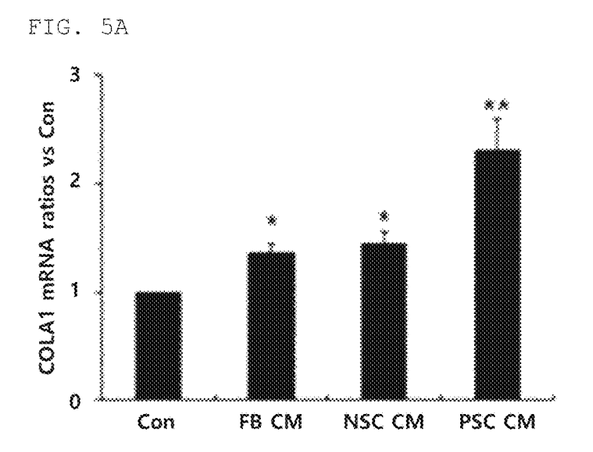
FIGS. 5A to 5D are diagrams for confirming effects of the conditioned mediums of egg-derived stem cells on expression of collagen genes.
Figure 5B:
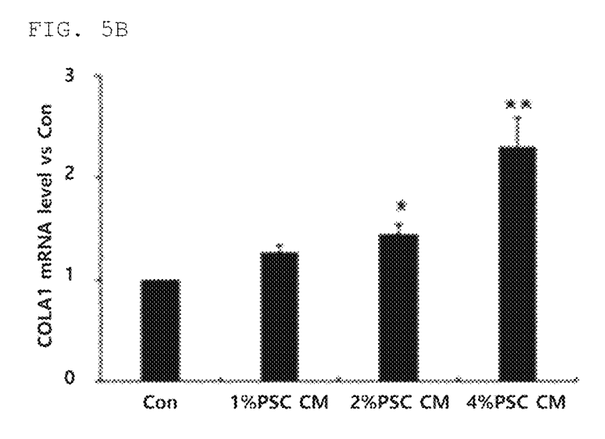
Figure 5C:
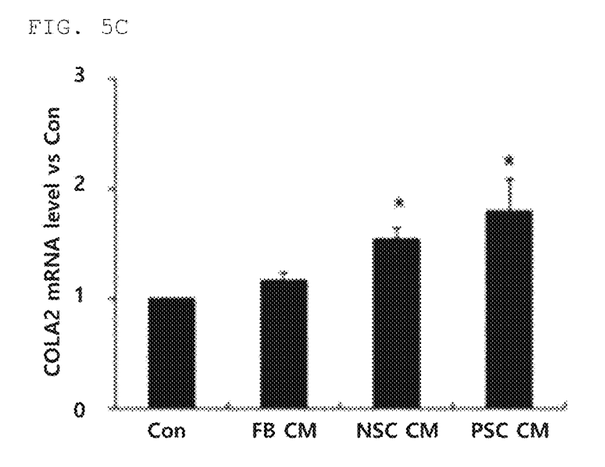
Figure 5D:
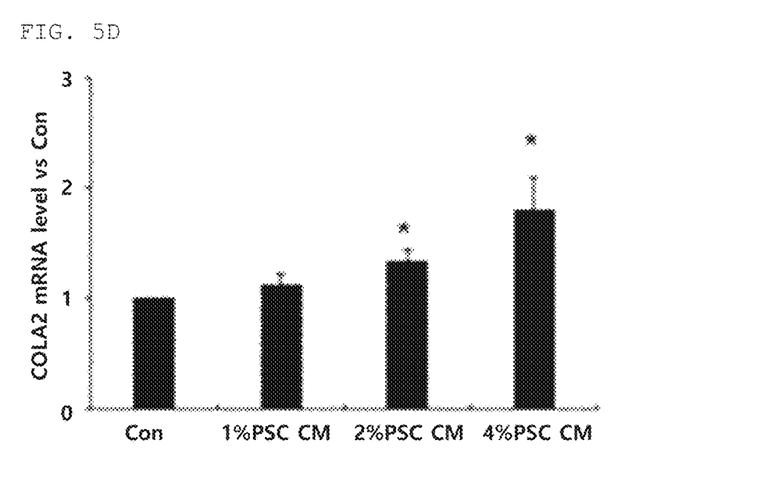
Figure 6A:
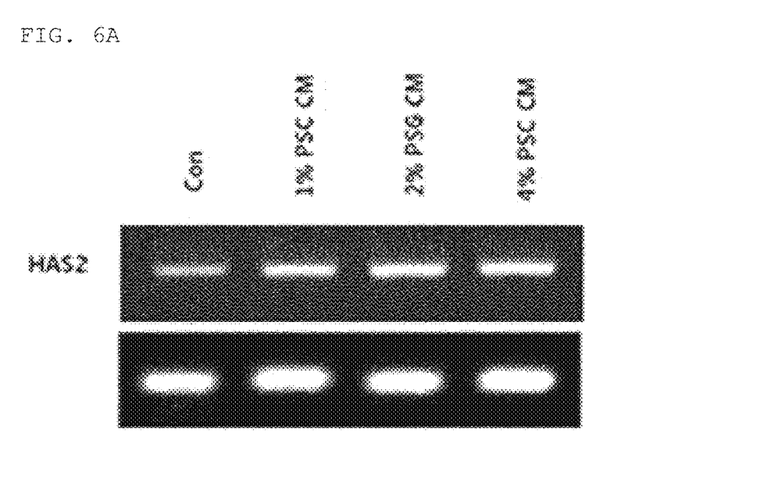
FIGS. 6A and 6B are diagrams for confirming effects of the conditioned mediums of egg-derived stem cells on HAS-2 expression and hyaluronic acid production amount.
Figure 6B:
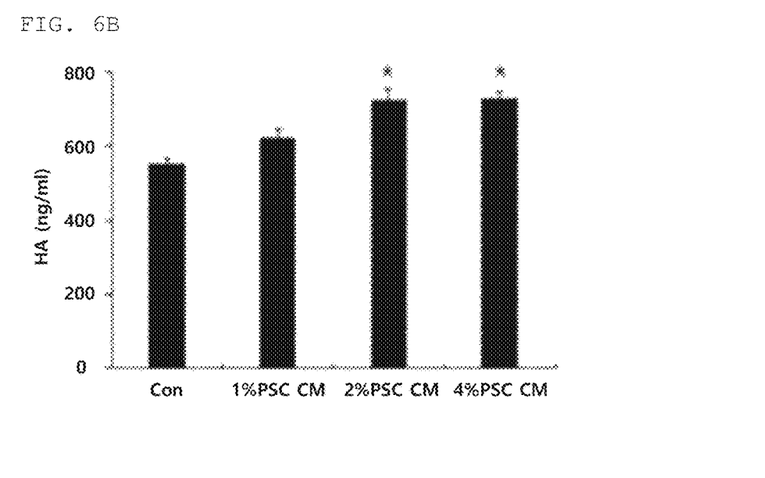

As a result, as shown in FIGS. 5A to 5D, it was confirmed that the mediums containing the conditioned medium of neural stem cells and the conditioned medium of pluripotent stem cells according to the present invention significantly increased the expression of the collagen genes relating to the wrinkle improvement compared with the control group and the mediums containing the fibroblast conditioned medium (FIGS. 5A and 5C). The addition amounts of the pluripotent stem cell conditioned mediums exhibiting the significant effects were reduced to confirm the collagen genes expression, and as a result, it was confirmed that the gene expression was significantly increased even in the addition concentration of 2% or less, compared with the control group (FIGS. 5B and 5D). As shown in FIGS. 6A and 6B, it was confirmed that the mediums containing conditioned mediums of the pluripotent stem cells according to the present invention significantly increased the HAS-2 expression and the hyaluronic acid production amounts (FIGS. 6A and 6B).

Figure 7A:
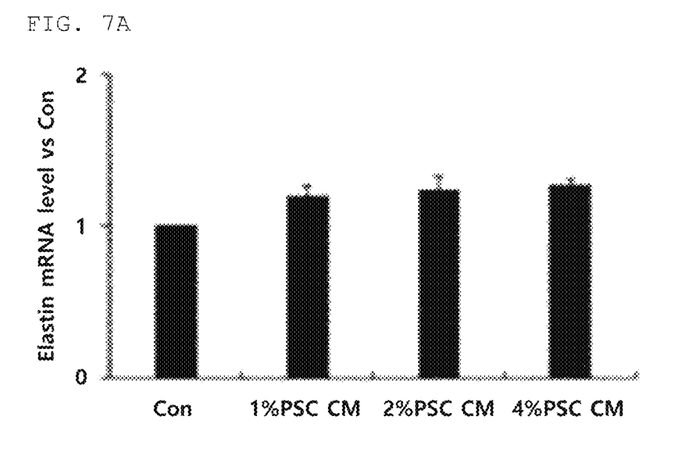
FIGS. 7A and 7B are diagrams for confirming the effect of the conditioned mediums of egg-derived stem cells on expression of elastin.
Figure 7B:
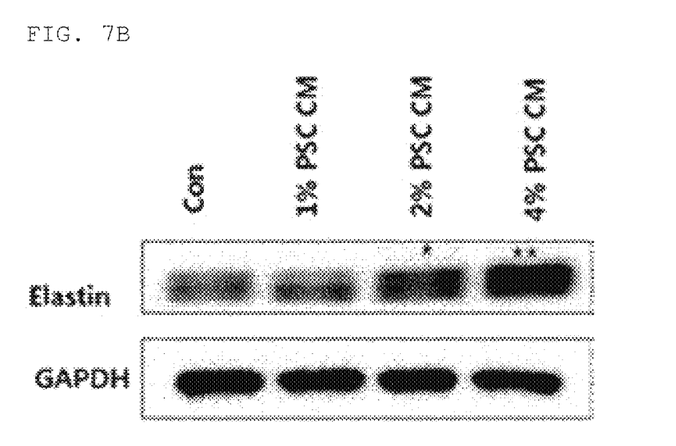

As shown in FIGS. 7A and 7B, it was confirmed that the medium containing the conditioned medium of the pluripotent stem cells according to the present invention significantly increased the expression of elastin relating to skin elasticity (FIGS. 7A and 7B).

Therefore, it was confirmed that the conditioned medium of neural stem cells and the conditioned medium of pluripotent stem cells according to the present invention exhibited significant skin regeneration and wrinkle improvement effects.

The invention claimed is:

1. A medium composition for cell proliferation comprising:
   a conditioned medium of chicken egg-derived stem cells,
   wherein the chicken egg-derived stem cells are neural stem cells isolated from a chicken egg cell,
   the conditioned medium is a medium in which the chicken egg-derived stem cells are cultured and then the cultured cells are removed, and
   the cell proliferation is for proliferation of human stem cells or skin cells.

2. The medium composition for cell proliferation according to claim 1,
   wherein the human stem cells are embryonic stem cells or adult stem cells.

3. The medium composition for cell proliferation according to claim 2,
   wherein the adult stem cells are skin-derived stem cells.

4. A method for treating a wound comprising:
a step of administering a medium composition according to claim 1 to the wound.

5. A method for skin regeneration or wrinkle improvement comprising:
a step of administering a medium composition according to claim 1 to an individual.

6. The method for skin regeneration or wrinkle improvement according to claim 5,
wherein the medium composition increases expression of a collagen gene and increases hyaluronic acid production.

7. The method for skin regeneration or wrinkle improvement according to claim 5,
wherein the medium composition increases expression of an elastin gene.

8. The method for skin regeneration or wrinkle improvement according to claim 5,
wherein the medium composition is formulated to any one selected from the group consisting of skin lotion, skin softener, skin toner, astringent, lotion, milk lotion, moisture lotion, nutrition lotion, massage cream, nutrition cream, moisture cream, hand cream, foundation, essence, nutrition essence, a pack, soap, cleansing foam, cleansing lotion, cleansing cream, body lotion, body cleanser, cleanser, treatment, liquid, beauty pack, an ointment, a gel, a liniment, liquid, a patch, and spray.

9. A cell proliferation method comprising:
a step of culturing cells with the medium composition of claim 1.

\* \* \* \* \*